(12) United States Patent
Davis et al.

(10) Patent No.: US 8,497,004 B2
(45) Date of Patent: *Jul. 30, 2013

(54) STERILIZED POLYETHERIMIDE ARTICLES

(75) Inventors: Scott Michael Davis, Pittsfield, MA (US); Robert R. Gallucci, Mt. Vernon, IN (US); Shawn Lee, Dalton, MA (US); Mark A. Sanner, Evansville, IN (US)

(73) Assignee: Sabic Innovative Plastics IP B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/486,435

(22) Filed: Jun. 1, 2012

(65) Prior Publication Data

US 2012/0308778 A1 Dec. 6, 2012

Related U.S. Application Data

(60) Provisional application No. 61/493,163, filed on Jun. 3, 2011.

(51) Int. Cl.
*B29D 22/00* (2006.01)

(52) U.S. Cl.
USPC .......................................... 428/34.1; 428/35.7

(58) Field of Classification Search
USPC .......... 428/34.1, 35.7; 528/353, 491; 525/420
See application file for complete search history.

(56) References Cited

U.S. PATENT DOCUMENTS

| | | |
|---|---|---|
| 3,803,085 A | 4/1974 | Takehoshi et al. |
| 3,847,867 A | 11/1974 | Heath et al. |
| 3,852,242 A | 12/1974 | White |
| 3,905,942 A | 9/1975 | Takekoshi et al. |
| 3,972,902 A | 8/1976 | Heath et al. |
| 3,983,093 A | 9/1976 | Williams, III et al. |
| 4,176,222 A | 11/1979 | Cinderey et al. |
| 4,293,670 A | 10/1981 | Robeson et al. |
| 4,443,591 A | 4/1984 | Schmidt et al. |
| 4,455,410 A * | 6/1984 | Giles, Jr. ....................... 525/436 |
| 4,473,684 A | 9/1984 | Maresca et al. |
| 4,503,168 A | 3/1985 | Hartsing, Jr. |
| 4,643,876 A | 2/1987 | Jacobs et al. |
| 5,037,902 A | 8/1991 | Harris et al. |
| 5,134,202 A | 7/1992 | Harris et al. |
| 5,212,259 A | 5/1993 | Harris et al. |
| 5,286,812 A | 2/1994 | Karasz et al. |
| 5,917,137 A | 6/1999 | Ekiner |
| 6,063,874 A | 5/2000 | Jin et al. |
| 6,077,480 A | 6/2000 | Edwards et al. |
| 6,482,880 B1 | 11/2002 | Rock |
| 7,041,773 B2 | 5/2006 | Gallucci et al. |
| 7,186,374 B2 | 3/2007 | Zelina et al. |
| 7,431,900 B2 | 10/2008 | Hill et al. |
| 7,902,316 B2 | 3/2011 | Johnson et al. |
| 2005/0113558 A1 | 5/2005 | Johnson et al. |
| 2006/0069236 A1 | 3/2006 | Brunelle et al. |
| 2007/0231201 A1 * | 10/2007 | Roberts et al. ................... 422/33 |
| 2007/0231202 A1 | 10/2007 | Roberts et al. |
| 2009/0018242 A1 | 1/2009 | Kailasam et al. |
| 2010/0185270 A1 | 7/2010 | Ramzipoor et al. |
| 2010/0285084 A1 | 11/2010 | Yang et al. |
| 2012/0149094 A1 * | 6/2012 | Smith et al. ................ 435/288.7 |

FOREIGN PATENT DOCUMENTS

| | | |
|---|---|---|
| EP | 0207417 A1 | 1/1987 |
| EP | 0440433 A2 | 8/1991 |
| EP | 1270018 A1 | 1/2003 |
| EP | 1728828 A1 | 12/2006 |
| WO | 03090796 A1 | 11/2003 |
| WO | 2009009525 A1 | 1/2009 |
| WO | 2012015608 A1 | 2/2012 |

OTHER PUBLICATIONS

U.S. Appl. No. 13/486,425; filed Jun. 1, 2012.
U.S. Appl. No. 61/493,140, filed Jun. 3, 2011.
International Search Report for International Application No. PCT/US2008/069404; International Filing Date Jul. 8, 2008; Date of Mailing Nov. 6, 2008; 6 pages.
Written Opinion of the International Search Report for International Application No. PCT/US2008/069404; International Filing Date Jul. 8, 2008; Date of Mailing Nov. 6, 2008; 5 pages.
International Search Report for International Application No. PCT/US2012/040443; International Filing date Jun. 1, 2012; Date of Mailing Aug. 17, 2012; 5 pages.
Written Opinion of the International Search Report for International Application No. PCT/US2012/040443; International Filing Date Jun. 1, 2012; Date of Mailing Aug. 17, 2012; 8 pages.
International Search Report for International Application No. PCT/US2012/040467; International Filing Date Jun. 1, 2012; Date of Mailing Sep. 4, 2012; 5 pages.
Written Opinion of the International Search Report for International Application No. PCT/US2012/040467; International Filing Date Jun. 1, 2012; Date of Mailing Sep. 4, 2012; 5 pages.

\* cited by examiner

*Primary Examiner* — N. Edwards
(74) *Attorney, Agent, or Firm* — Cantor Colburn LLP; Diderico van Eyl

(57) ABSTRACT

A sterilized article comprising a sterilized or hydrogen peroxide vapor-sterilized polymer composition, the polymer composition comprising a polyetherimide, wherein after exposure to 100 cycles of the hydrogen peroxide plasma sterilization using a mixture of hydrogen peroxide vapor and hydrogen peroxide plasma for 30 minutes at 20 to 55° C., the color of the polymer composition of the article exhibits a color shift of delta E of 10 units or less relative to the color of the polymer composition color before the first hydrogen peroxide plasma sterilization cycle, wherein delta E is measured in accordance with ASTM D2244.

22 Claims, No Drawings

STERILIZED POLYETHERIMIDE ARTICLES

CROSS REFERENCE TO RELATED APPLICATION

This application claims the benefit of U.S. Provisional Patent Application Ser. No. 61/493,163 filed Jun. 3, 2011, which is incorporated herein by reference herein in its entirety.

BACKGROUND

This disclosure relates to articles formed from polyetherimide compositions.

Hydrogen peroxide plasma sterilization devices are known, such as described in U.S. Pat. No. 4,643,876. The article to be sterilized is placed in the plasma chamber, the chamber is closed, and vacuum is drawn on the chamber to remove the gas that is in the chamber. An aqueous solution of hydrogen peroxide is typically injected into the chamber raising the pressure in the chamber to the desired level. The hydrogen peroxide remains in the chamber for a period of sufficient duration to allow the hydrogen peroxide to come in intimate contact with the item to be sterilized, before the plasma is generated at a power level sufficient to achieve sterilization. The power then remains on for the desired period to allow complete sterilization of the particular type of article being treated. As is known to those skilled in the art, the period of treatment will also vary depending upon the concentration of the hydrogen peroxide in the chamber and the amount of power that is applied to the chamber.

Hydrogen peroxide plasma sterilization devices are employed in health care facilities since they provide an easy and cost effective means of sterilizing healthcare devices prior to each use. Hydrogen peroxide plasma sterilization is an alternative to high temperature autoclave sterilization, especially for articles that include sensitive electronic or optical components that cannot be exposed to the high temperatures or moisture of an autoclave without becoming damaged. Hydrogen peroxide plasma sterilization systems operate at lower temperatures than high temperature autoclaves and achieve sterilization of articles through the antimicrobial action of peroxide plasma used instead of extreme temperature. In other instances a hydrogen peroxide vapor, that may contain little or no hydrogen peroxide plasma, may also be used for low temperature sterilization.

However, the adoption of hydrogen peroxide plasma sterilization has placed a new set of durability demands upon materials used to fabricate articles intended for repeated use in a sterile work environment, such as surgical devices of various types and configurations. Improvements in hydrogen peroxide plasma devices have increased the extent of diffusion of peroxide within the chamber, improving the ability to penetrate lumens and broadening the applicability of this technology to a wider range of instruments.

Plastic components that are exposed to repeated hydrogen peroxide plasma sterilizations are thus subjected to repeated rigorous challenges from the action of hydrogen peroxide plasma, an ionized acidic vapor, upon the surface of the molded article and through diffusion below the surface of the article. Retention of properties after exposure to repeated cycles of peroxide plasma sterilization is therefore needed.

There accordingly remains a need in the art for improved sterilized plastic articles that will endure repeated exposures to peroxide plasma sterilization.

SUMMARY OF THE INVENTION

As disclosed herein, an article comprises a sterilized polymer composition, the polymer composition comprising a polyetherimide, wherein after exposure to 100 cycles of the hydrogen peroxide plasma sterilization using a mixture of hydrogen peroxide vapor and hydrogen peroxide plasma for 30 minutes at 20 to 55° C., the color of polymer composition of the article exhibits a color shift of delta E of 10 units or less relative to the color of the polymer composition before the first hydrogen peroxide plasma sterilization cycle, wherein delta E is measured in accordance with ASTM D2244.

In another embodiment, the above article bears an etched marking on at least a portion of the above sterilized polymer composition, wherein the etching is legible when observed from a distance of 0.3 meters without magnification after the exposure of the article to 100 cycles of the hydrogen peroxide plasma sterilization.

In another embodiment, the above sterilized articles are, or are components of, medical devices, surgical devices, sterilization devices, decontamination devices, food handling devices, food preparation devices, beverage handling devices, beverage preparation devices, and combinations thereof.

DETAILED DESCRIPTION

The present inventors have discovered that sterilized articles comprising polyetherimide have a surprising and important feature, in that they retain their original appearance better than articles molded of polyphenylene ether sulfone.

In particular, such polyetherimide articles exhibit better color retention and retain etched surface markings better than articles molded from polyphenylene ether sulfone. These performance advantages allow sterilized articles molded from polyetherimide according as described herein to remain in service through more cycles of peroxide plasma sterilization and use in sterile work environments than articles molded from polyphenylene ether sulfone.

Various numerical ranges are disclosed in this patent application. Because these ranges are continuous, they include every value between the minimum and maximum values. Unless expressly indicated otherwise, the various numerical ranges specified in this application are approximations. The endpoints of all ranges directed to the same component or property are inclusive of the endpoint and independently combinable.

The terms "a" and "an" do not denote a limitation of quantity, but rather denote the presence of at least one of the referenced items. "Or" means "and/or." As used herein, "combination thereof" is inclusive of one or more of the recited elements, optionally together with a like element not recited. Reference throughout the specification to "an embodiment," "another embodiment," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

All molecular weights in this application refer to weight average molecular weights (Mw) unless indicated otherwise. All such mentioned molecular weights are expressed in Daltons.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. The term "alkyl" includes both $C_{1-30}$ branched and straight chain, unsaturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, s-pentyl, n- and s-hexyl, n- and s-heptyl, and, n- and s-octyl. The term "aryl" means an aromatic moiety containing the specified number of carbon atoms, such as to phenyl, tropone, indanyl, or naphthyl.

All ASTM tests are based on the 2003 edition of the Annual Book of ASTM Standards unless otherwise indicated.

Polyetherimides can comprise more than 1, typically 10 to 1000, or, more specifically, 10 to 500 structural units, of the formula (1)

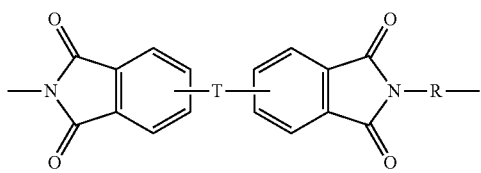

(1)

wherein R can be, for example substituted or unsubstituted divalent organic groups such as: (a) aromatic hydrocarbon groups having 6 to 24 carbon atoms and halogenated derivatives thereof; (b) straight or branched chain alkylene groups having 2 to 20 carbon atoms; (c) cycloalkylene groups having 3 to 24 carbon atoms, or (d) divalent groups of formula (2)

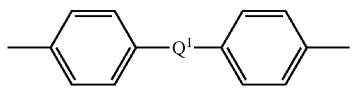

(2)

wherein $Q^1$ is selected from —O—, —S—, —C(O)—, —SO$_2$—, —SO—, and —C$_y$H$_{2y}$— and fluorinated derivatives thereof wherein y is an integer from 1 to 5. Examples of groups R include divalent groups of the following formulae (A)

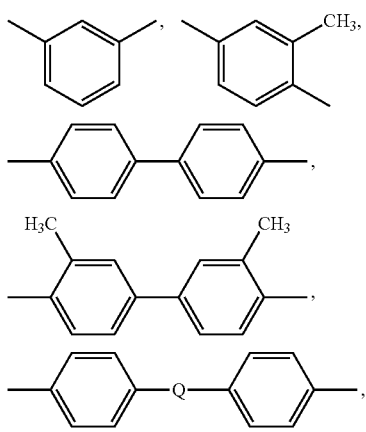

(A)

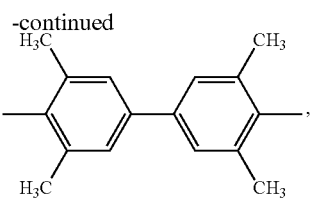

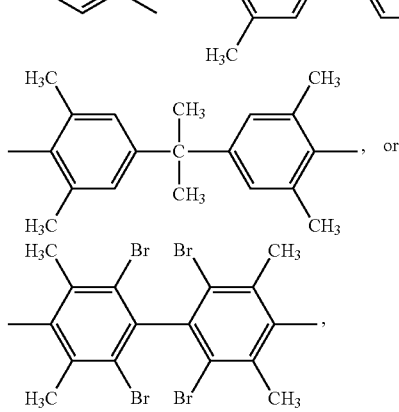

or combinations thereof, wherein Q is a divalent moiety selected from —O—, —C(O)—, —S—, $C_yH_{2y}$— (y being an integer from 1 to 5), and fluorinated derivatives thereof, including perfluoroalkylene groups. In a specific embodiment Q selected from —O—, —C(O)—, —C$_y$H$_{2y}$— (y being an integer from 1 to 5), and fluorinated derivatives thereof, including perfluoroalkylene groups.

Further in formula (1), T is —O— or a group of the formula —O—Z—O— wherein the divalent bonds of the —O— or the —O—Z—O— group are in the 3,3', 3,4', 4,3', or the 4,4' positions. Z includes, but is not limited to, substituted or unsubstituted divalent organic groups such as: (a) aromatic hydrocarbon groups having about 6 to about 20 carbon atoms and halogenated derivatives thereof; (b) straight or branched chain alkylene groups having about 2 to about 20 carbon atoms; (c) cycloalkylene groups having about 3 to about 20 carbon atoms, or (d) divalent groups of formula (3)

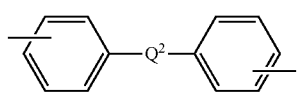

(3)

wherein $Q^2$ includes but is not limited to a divalent moiety selected from —O—, —C(O)—, —S—, $C_yH_{2y}$— (y being an integer from 1 to 5), and fluorinated derivatives thereof, including perfluoroalkylene groups. In a specific embodiment Q selected from —O—, —C(O)—, —C$_y$H$_{2y}$— (y being an integer from 1 to 5), and fluorinated derivatives thereof, including perfluoroalkylene groups.

In a specific embodiment the polyetherimide is a polymer of formula (1) wherein T is a group of the formula —O—Z—O— as described above. More specifically in Formula (1), R is a group of formula (A), specifically m-phenylene or p-phenylene, and Z is a group of formula (3), specifically a group derived from bisphenol A. In some embodiments, the polyetherimide can be a copolymer. Combinations of polyetherimides can also be used.

In some embodiments, the polyetherimide can be a copolymer. Combinations of polyetherimides can also be used.

The polyetherimide can be prepared by any of the methods well known to those skilled in the art, including the reaction of an aromatic bis(ether anhydride) of the formula (4)

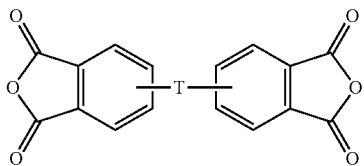

(4)

with an organic diamine of the formula (5)

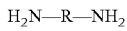

H₂N—R—NH₂ (5)

wherein T and R are defined as described above.

Examples of specific aromatic bis(ether anhydride)s and organic diamines are disclosed, for example, in U.S. Pat. Nos. 3,972,902 and 4,455,410. Illustrative examples of aromatic bis anhydrides include: 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride, as well as various combinations thereof. Another class of aromatic bis(ether anhydride)s included in formula (4) above includes, but is not limited to, compounds wherein T is of the formula (6)

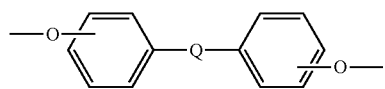

(6)

wherein the ether linkages are in the 4,4', 3,3', 3,4', or 4,3' positions, specifically the 4,4' positions, and Q is as defined above.

Examples of organic diamines include ethylenediamine, propylenediamine, trimethylenediamine, diethylenetriamine, triethylene tetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis(3-aminopropyl) amine, 3-methoxyhexamethylenediamine, 1,2-bis(3-aminopropoxy)ethane, bis(3-aminopropyl) sulfide, 1,4-cyclohexanediamine, bis-(4-aminocyclohexyl)methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl)methane, bis(2-chloro-4-amino-3,5-diethylphenyl)methane, bis(4-aminophenyl) propane, 2,4-bis(p-amino-t-butyl) toluene, bis(p-amino-t-butylphenyl)ether, bis(p-methyl-o-aminophenyl)benzene, bis(p-methyl-o-aminopentyl)benzene, 1,3-diamino-4-isopropylbenzene, bis(4-aminophenyl) sulfide, bis-(4-aminophenyl) sulfone, and bis(4-aminophenyl)ether. Combinations of these compounds can also be used. In some embodiments the organic diamine comprises m-phenylenediamine, p-phenylenediamine, sulfonyl dianiline, or combinations comprising one or more of the foregoing.

In an embodiment, the polyetherimide polymer comprises structural units according to formula (1) wherein each R¹ is independently p-phenylene or m-phenylene or a combination thereof and T is a divalent group of the formula (7)

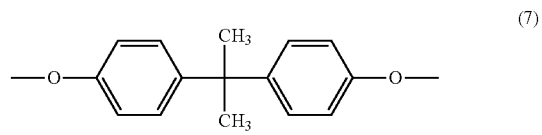

(7)

In this embodiment, the polyetherimide can have less than 5 ppm of free bisphenol A.

Included among the many methods of making polyetherimides are those disclosed in U.S. Pat. Nos. 3,847,867, 3,852,242, 3,803,085, 3905,942, 3,983,093, 4,443,591, and 7,041,773. These patents mentioned for the purpose of teaching, by way of illustration, general and specific methods for preparing polyimides. Some polyetherimide (PEI) materials are described in ASTM D5205-96 Standard Classification System for Polyetherimide Materials.

Polyetherimides can have a melt index of 0.1 to 10 grams per minute (g/min), as measured by American Society for Testing Materials (ASTM) D1238 at 340 to 370° C., using a 6.7 kilogram (kg) weight. In some embodiments, the polyetherimide polymer has a weight average molecular weight (Mw) of 1,000 to 150,000 grams/mole (Dalton), as measured by gel permeation chromatography, using polystyrene standards. In some embodiments the polyetherimide has Mw of 10,000 to 80,000 Daltons. Such polyetherimide polymers typically have an intrinsic viscosity greater than 0.2 deciliters per gram (dug), or, more specifically, 0.35 to 0.7 dl/g as measured in m-cresol at 25° C.

In an embodiment, the polyetherimide comprises less than 50 ppm amine end groups. In other instances the polymer will also have less than 5 ppm of free, unpolymerized bisphenol A (BPA).

The polyetherimides can have low levels of residual volatile species, such as residual solvent. In some embodiments, the polyetherimides have a residual volatile species concentration of less than 1000 parts by weight per million parts by weight (ppm), or, more specifically, less than 500 ppm, or, more specifically, less than 300 ppm, or, even more specifically, less than 100 ppm. In some embodiments, the composition has a residual volatile species concentration of less than 1000 parts by weight per million parts by weight (ppm), or, more specifically, less than 500 ppm, or, more specifically, less than 300 ppm, or, even more specifically, less than 100 ppm.

Examples of residual volatile species are halogenated aromatic compounds such as chlorobenzene, dichlorobenzenes, trichlorobenzenes, aprotic polar solvents such as dimethyl formamide (DMF), N-methylpyrrolidinone (NMP), dimethyl sulfoxide (DMSO), diaryl sulfones, sulfolane, pyridine, phenol, veratrole, anisole, cresols, xylenols, dichloro ethanes, tetra chloro ethanes, pyridine and mixtures thereof.

Low levels of residual volatile species in the final polymer product can be achieved by known methods, for example, by devolatilization or distillation. In some embodiments the bulk of any solvent can be removed and any residual volatile species can be removed from the polymer product by devolatilization or distillation, optionally at reduced pressure. In other embodiments, the polymerization reaction is taken to some desired level of completion in solvent and then the polymerization is essentially completed and most remaining water is removed during at least one devolatilization step following the initial reaction in solution. Apparatuses to devolatilize the polymer mixture and reduce solvent and other volatile species to the low levels needed for good melt processability are generally capable of high temperature heating under vacuum with the ability to rapidly generate high surface area to facilitate removal of the volatile species. The mixing portions of such apparatuses are generally capable of supplying sufficient power to pump, agitate, and stir the high temperature, polyetherimide melt which can be very viscous. Suitable devolatilization apparatuses include, but are not limited to, wiped films evaporators, for example those made by the LUWA Company and devolatilizing extruders, especially twin screw extruders with multiple venting sections, for example those made by the Coperion Company or Welding Engineers.

In some embodiments, the polyetherimide has a glass transition temperature of 200 to 280° C.

It is often useful to melt filter the polyetherimide using known melt filtering techniques to remove foreign material, carbonized particles, cross-linked resin, or similar impurities. Melt filtering can occur during initial resin isolation or in a subsequent step. The polyetherimide can be melt filtered in the extrusion operation. Melt filtering can be performed using a filter with a pore size sufficient to remove particles with a dimension of greater than or equal to 100 micrometers or with a pore size sufficient to remove particles with a dimension of greater than or equal to 40 micrometers.

The polyetherimide composition can optionally comprise additives such as UV absorbers; stabilizers such as light stabilizers and others; lubricants, plasticizers; pigments; dyes; colorants; anti-static agents; metal deactivators; and combinations comprising one or more of the foregoing additives. In some embodiments, the additive can include a combination of a mold release agent and a stabilizer selected from phosphite stabilizers, phosphonite stabilizers, hindered phenol stabilizers, and combinations thereof. In an embodiment, a phosphorus-containing stabilizer is used.

Antioxidants can be compounds such as phosphites, phosphonites, hindered phenols, or combinations thereof. Phosphorus-containing stabilizers including triaryl phosphites and aryl phosphonates are of note as useful additives. Difunctional phosphorus containing compounds can also be employed. In some embodiments, to prevent loss of the stabilizer during melt mixing or subsequent melt forming processes such as injection molding, the phosphorus containing stabilizers with a molecular weight greater than or equal to 300 Dalton, but less than or equal to 5,000 Dalton, are useful. The additive can comprise hindered phenols with molecular weight over 500 Dalton. Phosphorus-containing stabilizers can be present in the composition at 0.01 to 3.0% or to 1.0% by weight of the total composition.

The polyetherimide compositions can optionally comprise a mold-release agent. Examples of the mold-release agents include, but are not limited to, natural and synthetic paraffins, polyethylene waxes, fluorocarbons, and other hydrocarbon mold-release agents; stearic acid and other higher fatty acids; stearic acid amide, ethylene bis stearamide, and other fatty acid amides, alkylene bis fatty acid amides, and other fatty acid amide mold-release agents, stearyl stearate, pentaerythritol tetrastearate, and other alcohol esters of fatty acid, polyhydric alcohol esters of fatty acid, and other fatty acid ester mold release agents, silicone oil and other silicone mold release agents, and combinations of any of the aforementioned. In some embodiments, at least 0.5 weight percent, for example 0.05 to 5.0 weight percent, based on the total weight of the composition, of a mold release agent selected from $C_6$ to $C_{36}$ alkyl carboxylic esters, $C_6$ to $C_{36}$ alkyl carboxylic acids, $C_6$ to $C_{36}$ alkyl carboxylic acid salts, $C_6$ to $C_{36}$ aliphatic carboxylic amides, polyolefins, and combinations thereof are used.

A wide variety of colorants can be used, including dyes and pigments. For example, the polyetherimide/polyphenylene ether sulfone compositions can comprise from 0.1 to 10.0 weight percent of a colorant, for example a pigment such as pigments selected from rutile titanium dioxide, anatase titanium dioxide, coated titanium dioxide, passivated titanium dioxide, and encapsulated titanium dioxide. The titanium dioxide can have a particle size of from 0.1 to 10 micrometers. In some instances the pigment can also be carbon black, (for example pigment black 7), solvent red 52, solvent violet 36, solvent violet 13, pigment brown 24, pigment blue 29, pigment blue 15:4 or combinations thereof.

The composition may also contain a biocidal additive component, in particular antimicrobial additive component. Biocides for use in polymer compositions include metals, for example copper, silver, zinc, or combinations thereof, inorganic compounds such as silanes, and various organic compounds, which can be any of those known in the art, for example chlorinated phenols such as 5-chloro-2-(2,4-dichlorophenoxy)phenol), polyhexamethylene biguanide hydrochloride (PHMB), doxycycline, chlorhexidine, metronidazole, thymol, enalypol, methyl salicylate, and the like. Biocides as used herein include those classified as germicides, antimicrobials, antibiotics, antibacterials, antivirals, antifungals, antiprotozoals, antiyeast, antialgae, and antiparasites. Combinations of different biocides can be used, for example a combination of microparticulate or nanoparticulate silver or silver-containing compound (e.g., silver sulfate, silver zeolites, and silver functionalized clay) and a zinc oxide. The biocide is used in an amount effective to provide the desired activity, for example an amount from more than 0 to 5 weight percent of the total polymer composition. In some instances the biocide will be thermally stable at the polymer processing temperature of 300° C. or greater. Inorganic biocides are preferred.

The polyetherimide compositions can also comprise other polymers such as polysulfones, silicone polyetherimides, polyamides, polyphenylene ethers, polyolefins, and mixtures thereof, provided that they are used in such amounts as not to compromise the color stability, multiaxial impact energy, and tensile strength properties enumerated herein. In some embodiments, such polymers can be added to the composition in amounts of 1 to 40 weight percent, or, 1 to 30 weight percent, or, 1 to 20 weight percent, based on the total weight of the composition. In an embodiment, no other polymer is present.

The polyetherimide composition may include fillers or reinforcing agents. Where used, useful fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boronnitride powder, boron-silicate powders, or the like; oxides such as $TiO_2$, aluminum oxide, magnesium oxide, or the like; calcium sulfate; calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate or the like; organic fillers such as polytetrafluoroethylene; reinforcing organic fibrous fillers formed from organic polymers capable of forming fibers such as polyimide, polybenzoxazole, or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents. The fillers and reinforcing agents may be in the form of nanoparticles, that is, particles with a median particle size ($D_{50}$) smaller than 100 nanometers as determined using light scattering methods.

The polyetherimide composition can be prepared by melt mixing or a combination of dry blending and melt mixing. Melt mixing can be performed in single or twin screw type extruders or similar mixing devices that can apply a shear and heat to the components. Melt mixing can be performed at temperatures greater than or equal to the melting temperatures of the polyetherimides and less than the degradation temperatures of any of the components of the composition. In some embodiments suitable melt mixing is achieved at a temperature of 125 to 150° C. above the glass transition temperature of the polymer.

All of the ingredients can be added initially to the processing system. In some embodiments, the ingredients can be added sequentially or through the use of one or more master batches.

The compositions described above can be used to make articles (including portions of articles). Articles can be made by any suitable method, e.g., injection molding, film extrusion, compression molding, sintering, thermoforming, blow molding, profile extrusion, melt spinning, gas assist molding, foam molding, rotomolding, solvent casting, and the like. Articles can also comprise non-plastic parts such as metal and ceramic components such as screws, fasteners, inserts, blades, conductors, antennas, coatings and etc.

The articles can have a number of advantageous properties, in particular color stability. For example, after exposure to 100 cycles of hydrogen peroxide plasma sterilization using a mixture of hydrogen peroxide vapor and hydrogen peroxide plasma for 15 minutes at 20 to 55° C., the color of the polymer composition of the article (for simplicity, "the article") can exhibit a color shift delta E of 10 units or less, or 5 units or less, relative to the color of the article color before the first hydrogen peroxide plasma sterilization cycle, wherein delta E is measured in accordance with ASTM D2244. For example, after exposure to 100 cycles of hydrogen peroxide plasma sterilization using a mixture of hydrogen peroxide vapor and hydrogen peroxide plasma for 15 minutes at 20 to 55° C., the color of the article can exhibit a delta E of 0.5 to 10 units, 0.5 to 8 units, 0.5 to 6 units, 0.5 to 5 units, 0.5 to 4 units, or 0.5 to 2 units, relative to the color of the article color before the first hydrogen peroxide plasma sterilization cycle, wherein delta E is measured in accordance with ASTM D2244.

In another embodiment, the delta E of the article is 10 units or less or 5 units or less after exposure of the article to 100 to 200 sterilization cycles, wherein each cycle is from 10 to 60 minutes at 20 to 55° C. For example, after exposure to 100 to 200 cycles of hydrogen peroxide plasma sterilization using a mixture of hydrogen peroxide vapor and hydrogen peroxide plasma for 10 to 60 minutes at 20 to 55° C., the color of the article can exhibit a delta E of 0.5 to 10 units, 0.5 to 8 units, 0.5 to 6 units, 0.5 to 5 units, 0.5 to 4 units, or 0.5 to 2 units, relative to the color of the article color before the first hydrogen peroxide plasma sterilization cycle, wherein delta E is measured in accordance with ASTM D2244.

In still another embodiment, the delta E of an article comprising the polyetherimide/polyphenylene ether sulfone compositions is less than a delta E of another article comprising the same polymer composition without the polyetherimide, wherein each delta E is measured after exposure to 100 cycles of hydrogen peroxide plasma sterilization under the same conditions, for example 100 to 200 sterilization cycles, wherein each cycle is from 10 to 60 minutes, at 20 to 55° C.

The articles further resist surface erosion/abrasion that can arise during hydrogen peroxide plasma sterilization. In particular, the articles can have an etching on at least a portion of a surface of the polymer composition (for example for identification purposes). In some embodiments the etching is legible when observed from a distance of 0.3 meters without magnification after the exposure of the article to 100 cycles of hydrogen peroxide plasma sterilization under a variety of conditions, for example after exposure of the article to 100 to 200 sterilization cycles, wherein each cycle is from 10 to 60 minutes at 20 to 55° C. The articles' capacity to further resist surface abrasion with hydrogen peroxide plasma sterilization can also be evidenced by the capacity of the articles to retain their respective mass. In an embodiment, an article can retain at least 90% of its initial mass after the article has been exposed to 100 cycles of hydrogen peroxide plasma sterilization under a variety of conditions. In an embodiment, an article can retain at least 91%, 92%, 93%, 94%, 95%, 96%, 97%, 98%, 99%, 99.9% of its initial mass after the article has been exposed to 100 cycles of hydrogen peroxide plasma sterilization under a variety of conditions. Exemplary conditions include each cycle being from 10 to 60 minutes at 20 to 55° C., such as 15 minutes at 20 to 55° C.

Exemplary articles comprising the polyetherimide/polyphenylene ether sulfone composition include molded parts, sheets, slabs, profiles, films, or fibers. The articles can also include devices and components of devices such as medical devices, dental devices, sterilization devices, surgical devices, water purification devices, decontamination devices, and food and/or preparation and/or handling devices, such as part of a device or system for collecting, transporting, or handling beer, wine, milk, cheese, or other dairy products. Specific items include surgical instrument trays, handles, animal cages, bottles, cups, syringe bodies, endoscopes, ureteroscopes, catheters, clamps, cables, telescopes, forceps, scissors, drills, and the like.

Additional articles include, and are not limited to, stereo tactic equipment, defibrillator paddles, electrocautery instruments, esophageal dilators, laryngoscope blades, cryoprobes, dopplers, endoscopic instruments, fiberoptic light cables, laser hand pieces, fibers, and accessories, rigid and flexible endoscopes, cranial pressure transducer cables, trocar sheaths, video cameras and couplers, pigmentation hand pieces, resectoscope/working elements and sheaths, shaver hand pieces, surgical power equipment and batteries, ultrasound probes, ophthalmic lenses, patient lead cables, instrument tray mats, forceps, scissors, medical keyboard and mice, medical bags and pouches, and the like.

At least the following embodiments are within the scope of the above description.

Embodiment 1: A sterilized article comprising a sterilized polymer composition, the polymer composition comprising a polyetherimide, treated with a member selected from the group of hydrogen peroxide plasma, hydrogen peroxide vapor, and combinations thereof, the polyetherimide having less than 100 ppm amine end groups; wherein the polyetherimide has a weight average molecular weight of 10,000 to 80,000 Daltons; wherein the polyetherimide comprises repeating units of the formula The sterilized article of any of the preceding Embodiments, wherein the polyetherimide comprises repeating units of the formula

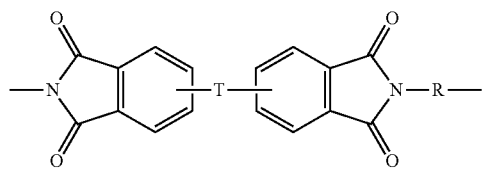

wherein R is a divalent radical of the formulae

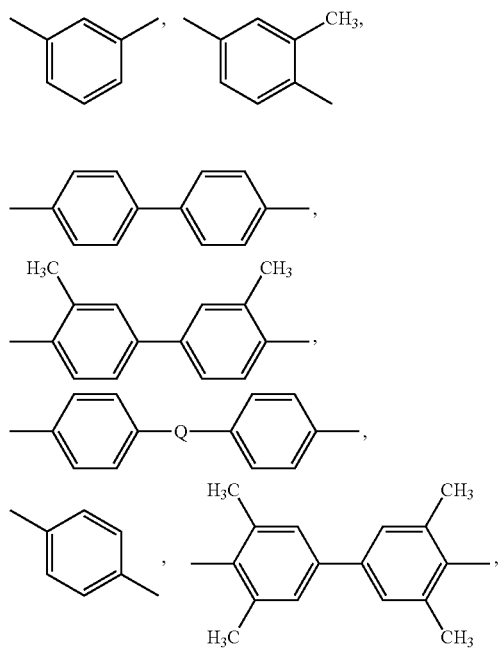

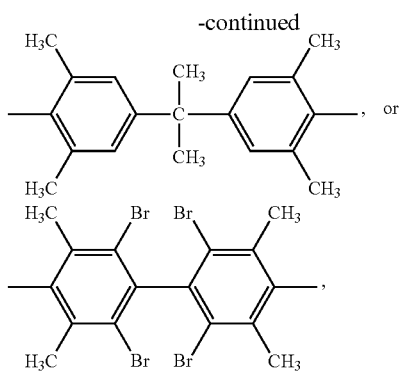

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is a divalent group of the formula

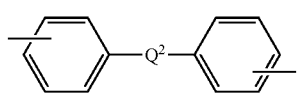

wherein Q$^2$ is selected from —O—, —S—, —C(O)—, —SO$_2$—, —SO—, and —C$_y$H$_{2y}$— wherein y is an integer from 1 to 5.

Embodiment 2: The sterilized article of Embodiment 1, wherein after exposure to 100 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the color of the polymer composition before the first hydrogen peroxide plasma sterilization cycle, wherein delta E is measured in accordance with ASTM D2244.

Embodiment 3: The sterilized article of Embodiment 2, wherein the delta E of the polymer composition after the exposure of the article to 100 cycles of hydrogen peroxide plasma sterilization is less than 5 units.

Embodiment 4: The sterilized article of Embodiment 1, wherein the delta E of the polymer composition is 10 units or less after exposure of the article to 100 to 200 sterilization cycles, wherein each cycle is from 10 to 60 minutes at 20 to 55° C.

Embodiment 5: The sterilized article of Embodiment 4, wherein the delta E of the polymer composition after the exposure is less than 5 units.

Embodiment 6: The sterilized article of any of the preceding Embodiments, wherein the article has a tensile strength at yield after 150 cycles of a treatment of a member selected from the group of hydrogen peroxide plasma, hydrogen peroxide vapor, and combinations thereof, is at least 12000 psi.

Embodiment 7: The sterilized article of any of the preceding Embodiments, wherein at least a portion of the polymer composition of the article has an etching, and wherein the etching is legible when observed from a distance of 0.3 meters without magnification after the exposure of the article to 100 cycles of hydrogen peroxide plasma sterilization.

Embodiment 8: The sterilized article of Embodiment 7, wherein the etching is legible when observed from a distance of 0.3 meters without magnification after exposure of the article to 100 to 200 sterilization cycles, wherein each cycle is from 10 to 60 minutes at 20 to 55° C.

Embodiment 9: The sterilized article of any of the preceding Embodiments, wherein the polyetherimide has less than 5 ppm of free bisphenol A.

Embodiment 10: The sterilized article of any of the preceding Embodiments, wherein the polyetherimide comprises less than 50 ppm amine end groups.

Embodiment 11: The sterilized article of any of the preceding Embodiments, wherein the polymer composition further comprises, based on the weight of the polymer composition, 0.1 to 10.0 weight percent of a colorant selected from rutile titanium dioxide, anatase titanium dioxide, coated titanium dioxide, passivated titanium dioxide, and encapsulated titanium dioxide, wherein the titanium dioxide has a particle size of from 0.1 to 10 micrometers.

Embodiment 12: The sterilized article of Embodiment 11, wherein the polymer composition further comprises a colorant selected from the group consisting of: carbon black, solvent red 52, solvent violet 36, solvent violet 13, pigment brown 24, pigment blue 29, pigment blue 15:4, or combinations thereof.

Embodiment 13: The sterilized article of any of the preceding Embodiments, wherein the polymer composition further comprises, based on the weight of the polymer composition, at least 0.01 weight percent of a phosphorous containing stabilizer having a molecular weight of at least 300 Daltons.

Embodiment 14: The sterilized article of Embodiment 13, wherein the phosphorous containing stabilizer is selected from aryl phosphites and aryl phosphonates.

Embodiment 15: The sterilized article of any of the preceding Embodiments, wherein the polymer composition further comprises, based on the weight of the polymer composition, at least 0.05 weight percent of a mold release agent selected from: C6 to C36 alkyl carboxylic esters, C6 to C36 alkyl carboxylic acids, C6 to C36 alkyl carboxylic acid salts, C6 to C36 alkyl amides, and polyolefins.

Embodiment 16: The sterilized article of any of the preceding Embodiments, wherein the article is selected from a molded part, sheet, slab, profile, film, and fiber.

Embodiment 17: The sterilized article of any of the preceding Embodiments, wherein the article is selected from a medical device, surgical device, sterilization device, decontamination device, food handling device, food preparation device, beverage handling device, beverage preparation device, or a component thereof.

Embodiment 18: The sterilized article of any of the preceding Embodiments, wherein the article is selected from a container, a syringe body, a tray, an animal cage, an endoscope, a ureteroscope, a catheter, a clamp, a cable, a telescope, forceps, scissors, and a drill.

Embodiment 19: The sterilized article of any of the preceding Embodiments, wherein the polymer composition further comprises a biocide.

Embodiment 20: The sterilized article of Embodiment 19, wherein the biocide is selected from metals, inorganic compounds, and organic compounds.

Embodiment 21: The sterilized article of Embodiment 19, wherein the biocide is selected from germicides, antimicrobials, antibiotics, antibacterials, antiyeasts, antialgals, antivirals, antifungals, antiprotozoals, antiparasites, and combinations thereof.

Embodiment 22: A sterilized article comprising a sterilized polymer composition, the polymer composition comprising a polyetherimide, treated with a member selected from the group of hydrogen peroxide plasma, hydrogen peroxide vapor, and combinations thereof; wherein the polyetherimide has a weight average molecular weight of 10,000 to 80,000 Daltons; wherein after exposure to 100 cycles of sterilization for 30 minutes at 20 to 55° C., the color of polymer composition of the article exhibits a color shift of delta E of 10 units or less relative to the color of the polymer composition before the first hydrogen peroxide sterilization cycle, wherein delta E is measured in accordance with ASTM D2244; wherein at least a portion of the sterilized polymer composition has an etching, wherein the etching is legible when observed from a distance of 0.3 meters without magnification after the exposure of the article to 100 cycles of the hydrogen peroxide sterilization.

The invention is further illustrated by the following non-limiting examples.

EXAMPLES

Materials

The materials employed to prepare samples for use in the Examples and Comparative Examples are identified in Table 1.

TABLE 1

| Material | Description | Source |
|---|---|---|
| PEI* | ULTEM 1000 Polyetherimide (Mw = 55,000 (GPC, PS standards), refractive index = 1.6586 (measured at 633 nanometers and 23° C.), Tg = 221° C.) PEI, amine end groups less than 20 ppm | SABIC Innovative Plastics |
| PPSU | RADEL R5100 Polyphenylene Ether Sulfone (Mw = 49,600 (GPC, PS standards), refractive index = 1.6673 (measured at 633 nanometers at 23° C.), Tg = 224° C.) | Solvay Co. |
| Solvent Red 52 | 3-Methyl-6-(p-toluidino)-3H-dibenz[f,ij]isoquinoline-2,7-dione | Lanxess |
| Solvent Violet 36 | 1,8-bis-(p-toluidino)-9,10-anthraquinone | Lanxess |
| Solvent Violet 13 | 1-hydroxy-4-(p-toluidino)-9,10-anthraquinone | Lanxess |
| Titanium Dioxide | Pigment White 6, a rutile silica-alumina encapsulated TiO$_2$ (0.24 micron diameter) | DuPont |
| Pigment Brown 24 | Chrome Antimony Titanium Brown | BASF |
| Pigment Blue 29 | Ultramarine Blue | Lanxess |
| Pigment Black 7 | Carbon Black | Cabot |
| Pigment Blue 15:4 | Copper Phthalocyanine Blue | Sun Chemical |

*contains 0.1 weight percent tris (di-2,4-tert butyl phenyl) phosphite (IRGAPHOS 168)

Techniques and Procedures

Blends were prepared by extruding of mixtures of the polyphenylene ether sulfone or polyetherimide in a 2.5 inch (63.5 mm) single-screw vacuum vented extruder. Compositions are listed in weight percent based on the total weight of the composition except where noted otherwise. The extruder was set at about 325 to 360° C. The blends were run at about 180 rotations per minute (rpm) under vacuum using a mild mixing screw; vacuum was approximately 20 inches (508 mm) of mercury (Hg). In some instances the blend was melt filtered using a 40 micrometers filter. The extrudate was cooled, pelletized, and dried at 135° C. Test samples were injection molded at a set temperature of 350 to 375° C. and mold temperature of 150° C., a screw speed of approximately 60 rpm, with 50 psi (0.345 MPa) back pressure using a 30 seconds cycle time.

Gel permeation chromatography (GPC) was done as per ASTM D5296, polystyrene standards were used for calibration. Tensile strength was measured on injection molded bars as per ASTM D638 at 0.2 inches (12.7 mm)/minute crosshead speed. Tensile strength is reported at yield (Y) and break (B), percent elongation (% E) is reported at break. Weight loss was measured by comparing the weight of bars before and after 150 and 300 hydrogen peroxide plasma sterilization cycles using an analytical balance accurate to at least 0.01 grams. The reported value is an average of at least 4 samples. Percent transmission (% T) was measured on 3.2 mm thick injection molded parts as per ASTM D1003 using a D65 illuminant with a 10 degree observer angle. Multiaxial impact (MAI) was run on 3.2×102 mm injection molded discs as per ASTM 56280-10 the total energy is reported as Joules (J) and foot-pounds (ft-lbs). Glass transition temperature (Tg) was measured by DSC on the second scan using a heating rate of 20° C./min.

Color Chip Sterilization Testing—Test chips were loaded and cycled in a STERRAD® NX hydrogen peroxide sterilization chamber (manufactured by Advanced Sterilization Products, a division of Ethicon, Inc.) to evaluate the materials ability to retain its color. The materials were run for the indicated number of sterilization cycles and then removed for evaluation. Each cycle consisted of 2 stages for a total time of 30 minutes at a temperature at 20 to 55° C. with at least 4 minutes exposure to a hydrogen peroxide derived gas plasma per stage. Each stage of a cycle comprised a 0.5 min. injection, 7.0 minute transfer, 0.5 min diffusion and a 4.0 minute plasma exposure. The injection volume of 53 wt. % aqueous hydrogen peroxide was 1800 uL.

The hydrogen peroxide vapor exposure was done using a AMSCO V-PRO low temperature sterilization system by STERIS Co. The sterilization cycle comprises a conditioning phase where a vacuum pulse is used to remove air and moisture from the chamber followed by a sterilization phase where a hydrogen peroxide vapor is drawn and held in the chamber in a series of vacuum pulses and is in contact with the article (at least a portion of which comprises a PEI resin). The temperature varied from 20 to 50° C. After a programmed time, the vapor is removed and the chamber aerated and brought to atmospheric pressure.

The STERRAD NX, 100NX and STERIS AMSCO V-PRO sterilization systems both employ hydrogen peroxide as the sterilant. The STERRAD NX concentrates liquid hydrogen peroxide to form a hydrogen peroxide vapor that is at least partially in a plasma form. The STERIS V-PRO Sterilizer forms a hydrogen peroxide vapor with little or no plasma.

A spectrophotometer was used at a 10 degree observation angle under illumination at a 65 degree angle to measure color indices (L*, a*, b*) of each color chip, at three reported points in time: as molded; 100 cycles; and 150 cycles. The changes in value of (L*, a*, b*) over the reported number of cycles are determined (dL, da, db) and then squared and summed, and the square root of the result is taken $((dL^2+da^2+db^2)^{1/2}$ delta E) to produce the value reported under delta E. Color was measured using a COLOREYE 7000A instrument from GretagMacbeth as per ASTM D2244. In addition, a gloss meter was used to evaluate surface gloss at 60, and 85 degrees as per ASTM method D 52308 and reported in gloss units.

Color coordinates, transmittance, and haze were determined using a MacBeth CE7000 spectrophotometer. This instrument uses a Xenon flash light source. Wavelength monitoring and detection range is from 360 nm to 760 nm. CIELab color coordinates for opaque and translucent samples are calculated assuming illuminate D65 and 10 degree observer. Transmittance is the Y color coordinate in the 1931 tristimulus scale—illuminate C & 2 degree observer. Haze is the % scattered light/total transmission. This is determined in a two-step measurement sequence using a white standard and a light trap. Transmittance and haze measurements apply to translucent samples only. Gloss measurements on opaque samples were made with a BYK Gardner micro Tri-glossmeter.

Examples 1-3 and Comparative Examples A-C

These materials were combined in the proportions specified in Table 2 to produce the six classes of experimental samples identified. Note that the PPSU and PEI/PPSU blends were formulated (color matched) so that the resultant articles had the same white, gray or blue colors as molded.

TABLE 2

| Color Formulations | g/lb of resin (g/0.454 kg) | |
| --- | --- | --- |
| White | Ex. 1 | Comp. Ex. A |
| Resin | PEI | PPSU |
| Solvent Red 52 | 0.012 | 0.0045 |
| Titanium Dioxide | 46.5 | 33.0 |
| Pigment Brown 24 | none | 0.155 |
| Pigment Blue 29 | 0.42 | 0.35 |
| Gray | Ex. 2 | Comp. Ex. B |
| Resin | PEI | PPSU |
| Solvent Violet 36 | 0.05 | 0.027 |
| Titanium Dioxide | 18.0 | 18.0 |
| Pigment Black 7 | 0.09 | 0.09 |
| Pigment Blue 29 | 0.40 | 0.50 |
| Pigment Brown 24 | 0.40 | 0.5 |
| Blue | Ex. 3 | Comp. Ex. C |
| Resin | PEI | PPSU |
| Solvent Violet 13 | 0.20 | 0.16 |
| Titanium Dioxide | 6.2 | 5.15 |
| Pigment Blue 15:4 | none | 0.33 |
| Pigment Brown 24 | 0.36 | 0.20 |

Examples 1, 2, and 3 are compositions which contain polyetherimide, along with the other listed ingredients in the indicated amounts measured in grams per pound of resin. Comparative Examples A, B and C contain polyphenylene ether sulfone, along with the other listed ingredients in the indicated amounts measured in grams per pound of resin. Together these samples present comparisons of pigmented polyetherimide compositions against a similarly pigmented polyphenylene ether sulfone composition: Example 1 and Comparative Example A are white; Example 2 and Comparative Example B are gray; and Example 3 and Comparative Example C are blue.

These samples were evaluated according to the stated procedures and results are reported in Table 3.

TABLE 3

Color and Gloss vs. Peroxide Plasma Exposure

| Example | Description | Delta E | L* | a* | b* | 60 Degree Gloss | 85 Degree Gloss |
|---|---|---|---|---|---|---|---|
| Comp. Ex. A | PPSU - white as molded | 0.0 | 86.8 | -2.0 | -1.4 | 106.7 | 97.7 |
| | PPSU - white 100 cycles | 25.8 | 82.4 | 0.5 | 23.9 | 4.3 | 59.9 |
| | PPSU - white 150 cycles | 37.3 | 78.3 | 5.9 | 34.1 | 4.0 | 46.4 |
| | PPSU - white 200 cycles | 36.3 | 77.6 | 6.5 | 32.7 | 1.5 | 2.6 |
| | PPSU - white 300 cycles | 36.4 | 78.5 | 5.8 | 33.2 | 1.4 | 1.1 |
| Comp. Ex. B | PPSU - gray as molded | 0.0 | 66.6 | -1.0 | -2.0 | 106.7 | 97.8 |
| | PPSU - gray 100 cycles | 13.9 | 66.4 | -1.2 | 11.9 | 24.8 | 76.1 |
| | PPSU - gray 150 cycles | 25.6 | 64.6 | 1.4 | 23.4 | 3.5 | 46.2 |
| | PPSU - gray 200 cycles | 27.2 | 63.9 | 2.6 | 24.9 | 1.5 | 15.5 |
| | PPSU - gray 300 cycles | 33.6 | 61.7 | 4.5 | 30.8 | 1.1 | 1.6 |
| Comp. Ex. C | PPSU - blue as molded | 0.0 | 52.7 | -12.1 | -24.5 | 107.1 | 96.4 |
| | PPSU - blue 100 cycles | 24.7 | 53.5 | -14.1 | 0.1 | 33.9 | 85.1 |
| | PPSU - blue 150 cycles | 40.6 | 54.5 | -9.9 | 16.0 | 19.1 | 69.6 |
| | PPSU - blue 200 cycles | 37.3 | 51.6 | -12.8 | 12.8 | 0.9 | 2.8 |
| | PPSU - blue 300 cycles | 50.6 | 52.7 | -12.1 | -24.5 | 0.8 | 1.5 |
| Ex. 1 | PEI - white as molded | 0.0 | 87.2 | -2.5 | -1.0 | 92.6 | 89.7 |
| | PEI - white 100 cycles | 0.7 | 87.9 | -2.3 | -1.1 | 68.8 | 91.0 |
| | PEI - white 150 cycles | 0.8 | 87.7 | -2.6 | -0.4 | 29.8 | 77.0 |
| | PEI - white 200 cycles | 1.8 | 87.6 | -2.9 | 0.7 | 46.9 | 83.7 |
| | PEI - white 250 cycles | 1.3 | 87.7 | -2.7 | 0.2 | | 87.3 |
| | PEI - white 300 cycles | 1.3 | 87.9 | -2.8 | 0.0 | 6.8 | 63.8 |
| Ex. 2 | PEI - gray as molded | 0.0 | 66.5 | -1.2 | -1.8 | 108.1 | 97.9 |
| | PEI - gray 100 cycles | 1.3 | 67.8 | -1.3 | -1.8 | 69.9 | 92.8 |
| | PEI - gray 150 cycles | 1.9 | 68.2 | -1.4 | -1.1 | | 96.1 |
| | PEI - gray 200 cycles | 2.8 | 69.0 | -1.6 | -0.7 | 11.2 | 65.2 |
| | PEI - gray 250 cycles | 3.0 | 69.2 | -1.5 | -0.6 | 8.5 | 77.4 |
| | PEI - gray 300 cycles | 3.2 | 69.5 | -1.5 | -0.7 | 6.7 | 66.5 |
| Ex. 3 | PEI - blue as molded | 0.0 | 52.9 | -12.2 | -25.0 | 108.4 | 98.9 |
| | PEI - blue 100 cycles | 0.4 | 53.0 | -12.6 | -24.8 | 67.1 | 91.6 |
| | PEI - blue 150 cycles | 1.3 | 52.8 | -12.3 | -23.7 | 51.4 | 88.2 |
| | PEI - blue 200 cycles | 2.1 | 53.0 | -12.6 | -22.9 | 36.8 | 84.5 |
| | PEI - blue 250 cycles | 1.8 | 53.0 | -12.5 | -23.2 | 8.0 | 73.8 |
| | PEI - blue 300 cycles | 1.7 | 52.5 | -12.9 | -23.5 | 14.1 | 73.6 |

The PEI compositions demonstrate strong performance in retaining color after repeated sterilization in peroxide plasma and showed a significant improvement in color stability compared to PPSU after 100, 150, 200, 250 and 300 peroxide plasma sterilization cycles. Large delta E shifts were observed after 100 cycles for PPSU samples of Comparative Examples A (25.8), B (25.6) and C (24.7), as compared to the surprisingly much lower delta E shifts observed in the PEI compositions: Example 1 (0.7), Example 2 (1.3) and Example 3 (0.4), respectively. Higher numbers of sterilization cycles give even greater differences in color shift between the PPSU Comparative Examples and the PEI resin.

A large increase in delta E is a numerical representation of extent of color change, with 0 being a "no-change" condition.

Example 4 and Comparative Example D

Test chips were prepared from unpigmented, natural color polyimide resin according to the invention, referred to as Example 4 (PEI); and unpigmented, natural color polyphenylene ether sulfone, referred to as Comparative Example D (PPSU). These samples were exposed to 100, 150, 200 and 300 cycles of peroxide plasma sterilization, evaluated and the results are reported in Table 4.

TABLE 4

Color, Haze and Transmission vs. Peroxide Plasma Exposure

| | Example | |
|---|---|---|
| Composition | Comp. Ex. D PPSU uncolored | EX. 4 PEI uncolored |
| Delta E as molded | 0.0 | 0.0 |
| Delta E 100 cycles | 10.0 | 4.9 |
| Delta E 150 cycles | 16.6 | 5.5 |
| Delta E 200 cycles | 24.1 | 6.4 |
| Delta E 300 cycles | 34.4 | 6.6 |
| % Haze as molded | 5.1 | 2.6 |
| % Haze 100 cycles | 83.7 | 18.7 |
| % Haze 150 cycles | 91.7 | 27.3 |
| % Haze 200 cycles | 98.5 | 25.9 |
| % Haze 300 cycles | 99.6 | 68.0 |
| % T as molded (3.2 mm) | 68.7 | 47.8 |
| % Retention % T 100 cycles | 83.6 | 100.0 |
| % Retention % T 150 cycles | 76.9 | 100.0 |
| % Retention % T 200 cycles | 78.9 | 100.0 |
| % Retention % T 300 cycles | 64.6 | 100.0 |
| % T as molded | 68.7 | 47.8 |
| % T 100 cycles | 57.4 | 55.1 |
| % T 150 cycles | 52.8 | 55.9 |
| % T 200 cycles | 54.2 | 57.0 |
| % T 300 cycles | 44.4 | 57.3 |

The PPSU Comparative Example D shows a rapid yellowing with a delta E value of 24.1 after 200 cycles, there is also a loss of the initial transmission (dropping to 78.9% of the initial value) as well as a very large increase in haze going from 5.1 to 98.5% haze with the initially clear PPSU part becoming opaque. The PEI resin of Example 4 has delta E value after 200 cycles of 6.4 with 100% retention of transmission.

Table 5 shows the changes in mechanical properties, weight average molecular weight (Mw) of the polymer and the change in weight of the molded parts for Example 4 (PEI) and Comparative Example D (PPSU) after 150 and 300 peroxide plasma sterilization cycles.

TABLE 5

Mechanical Properties, Mw & Wt. Loss vs. Peroxide Plasma Exposure

| | Example | |
|---|---|---|
| Composition | Comp. Ex. D PPSU uncolored | EX. 4 PEI uncolored |
| T. Mod as molded psi | 318000 (2192.5 MPa) | 454000 (3130.2 MPa) |
| T. Str (Y) as molded psi | 11000 (75.8 MPa) | 14900 (102.7 MPa) |
| T. Str (B) as molded psi | 10300 (71.0 MPa) | 12200 (84.1 MPa) |
| Elong. (B) as molded % | 92 | 62 |
| T. Str (Y) 150 cycles psi | 10480 (72.3 MPa) | 14890 (102.7 MPa) |
| T. Str (B) 150 cycles psi | 8380 (57.8 MPa) | 11700 (80.7 MPa) |
| Elong. (B) 150 cycles % | 12 | 49 |
| MAI Total Energy J as molded | 61.9 | 51.5 |
| MAI Total Energy J 150 cycles | 15.0 | 31.4 |
| MAI Total Energy J 300 cycles | 4.6 | 25.4 |
| Mw as molded | 49,064 | 50,795 |
| Mw 150 cycles | 47,841 | 50,667 |
| Mw 300 cycles | 46,991 | 50,744 |
| % wt loss 150 cycles | 2.09 | 0.50 |
| % wt loss 300 cycles | 8.25 | 0.63 |

T. Str = tensile strength;
T. mod = tensile modulus

The unpigmented, natural color PEI sample, Example 4, demonstrated superior retention of tensile properties starting with a tensile strength at yield of 14,900 psi only dropping after 150 cycles to 14,890 psi, the PPSU comparative Example D had an initial tensile strength at yield of 11,000 psi (75.8 MPa) dropping to 10,480 psi (72.3 MPa). Percent elongation at break after for the PEI was 49% after 150 sterilization cycles while the PPSU sample dropped to 12%. Sample 4 also showed superior retention of its initial Mw after 150 and 300 cycles vs. the PPSU Comparative Example D. Comparative Example D has higher initial multiaxial impact. (MAI total energy=61.9 J) than the PEI of Example 4 but loses most of its total impact energy after 150 and 300 peroxide plasma sterilization cycles (MAI=15.0 and 4.6 J). Example 4 has a higher MAI total energy after 150 and 300 cycles of 31.4 and 25.4 J. The Comparative Example D further shows a weight loss after 150 and 300 cycles of 2.09 and 8.25% while the PEI resin of Example 4 shows less than 1% wt. loss. The PEI sample had a Tg of 218° C. The GPC analyses of Example 4 show that the PEI had a drop in weight average in molecular weight (Mw) of only 51 Daltons after 300 sterilization cycles compared to the PPSU control, example D which had a drop of 2073 Daltons.

Markings were etched into the surface of all samples with a metal stylus before sterilization. However, after 150 cycles, the etched markings were gone from the surface of the PPSU samples of Comparative Example D, while the PEI samples, example 4, retained their etched identifying markings.

The samples of Example 4 thus exhibited surprisingly better overall condition after 150 cycles of peroxide plasma sterilization than the PPSU samples. In addition, the PPSU samples had discolored toward red/orange while the samples of Example 4 retained their appearance.

Examples 5-7 and Comparative Examples E-G

The colored compositions of Table 2 were exposed to 200 and 300 cycles of hydrogen peroxide vapor sterilization in a STERIS AMSCO V-PRO low temperature (20 to 50° C.) sterilization system using a 55 minute cycle (the "Lumen Cycle" using 59% hydrogen peroxide). Hydrogen peroxide vapor is a milder sterilization technique than hydrogen peroxide plasma. The Comparative Examples E, F, and G, white, gray, and blue PPSU showed a large color of 29.3, 10.2 and 46.4 delta E after 300 cycles. PEI in the same colors, Examples 5, 6 and 7, showed color changes of only 1.3, 2.2, and 1.1 delta E, changes barely perceptible to human vision.

TABLE 6

Color vs. Peroxide Vapor Exposure

| Example | Description | Delta E | L* | a* | b* |
|---|---|---|---|---|---|
| Comp. Ex. E | PPSU - white as molded | 0.0 | 87.1 | −2.5 | −0.7 |
| | PPSU - white 200 cycles | 4.5 | 87.2 | −3.2 | 3.8 |
| | PPSU - white 300 cycles | 29.3 | 81.1 | 3.9 | 27.2 |
| Comp. Ex. F | PPSU - gray as molded | 0.0 | 66.7 | −1.0 | −2.0 |
| | PPSU - gray 200 cycles | 1.5 | 67.3 | −1.3 | −0.6 |
| | PPSU - gray 300 cycles | 10.2 | 67.2 | −1.3 | 8.2 |
| Comp. Ex. G | PPSU - blue as molded | 0.0 | 52.2 | −11.0 | −25.9 |
| | PPSU - blue 200 cycles | 20.2 | 53.7 | −16.1 | −6.4 |
| | PPSU - blue 300 cycles | 46.4 | 57.4 | −2.4 | 19.4 |
| Ex. 5 | PEI - white as molded | 0.0 | 87.2 | −2.3 | −0.6 |
| | PEI - white 200 cycles | 1.2 | 87.7 | −2.1 | −1.7 |
| | PEI - white 300 cycles | 1.3 | 87.8 | −2.1 | −1.7 |
| Ex. 6 | PEI - gray as molded | 0.0 | 66.6 | −1.4 | −2.1 |
| | PEI - gray 200 cycles | 1.7 | 68.3 | −1.5 | −2.2 |
| | PEI - gray 300 cycles | 2.2 | 68.8 | −1.5 | −2.0 |
| Ex. 7 | PEI - blue as molded | 0.0 | 52.9 | −12.7 | −24.2 |
| | PEI - blue 200 cycles | 0.3 | 53.0 | −12.5 | −24.4 |
| | PEI - blue 300 cycles | 1.1 | 52.4 | −11.8 | −24.6 |

Examples 8 and 9 and Comparative Examples H and I

Table 7 shows retention of multiaxial impact (MAI), tensile strength at yield and % elongation at break for unpigmented, clear PPSU (Comparative Example H) and PEI (Example 8) after 150 and 300 cycles hydrogen peroxide vapor exposure. After 300 cycles the PPSU sample has only 13% elongation and has a brittle MAI failure with a total impact energy of only 12.8 ft-lbs (17.4 J). The PEI article after 300 sterilization cycles has elongation at break of 86% with a MAI total impact energy of 30.5 ft-lbs (41.4 J).

TABLE 7

Mechanical Properties vs. Peroxide Vapor Exposure

| Example | Description | MAI Total Energy Ft-lbs | MAI Total Energy J | Tensile Str. (Y) psi (MPa) | % Elong @ Break |
|---|---|---|---|---|---|
| Comp. Ex. H | PPSU as molded | 57.0 | 77.3 | 11990 (82.7) | 105 |
| | PPSU 150 cycles | 63.8 | 86.5 | 10430 (71.9) | 100 |
| | PPSU 300 cycles | 12.8 | 17.4 | 10020 (69.1) | 13 |
| Ex. 8 | PEI as molded | 38.7 | 52.4 | 14800 (102.0) | 93 |

TABLE 7-continued

Mechanical Properties vs. Peroxide Vapor Exposure

| Example | Description | MAI Total Energy Ft-lbs | MAI Total Energy J | Tensile Str. (Y) psi (MPa) | % Elong @ Break |
|---|---|---|---|---|---|
| | PEI 150 cycles | 31.4 | 42.6 | 14840 (102.3) | 91 |
| | PEI 300 cycles | 30.5 | 41.4 | 14710 (101.4) | 86 |

Table 8 shows the changes in color, % haze and % transmission after exposure of unpigmented, clear PPSU (Comparative Example I) and PEI (Example 9) to 150 and 300 cycles hydrogen peroxide vapor sterilization. After 300 sterilization cycles the PPSU resin undergoes a strong yellowing (Delta E=38.3) with the formation of 22.5% haze and a drop in % transmission to 53.1%. Example 9, the sterilized polyetherimide (PEI) article, has a Delta E color shift of only 2.5, a % haze of 3.3% and a % transmission at 3.2 mm thickness of above 70%.

TABLE 8

Appearance vs. Peroxide Vapor Exposure

| Example | Description | L* | a* | b* | Delta E | % Haze | % Transmission |
|---|---|---|---|---|---|---|---|
| Comp. Ex. I | PPSU as molded | 85.2 | 0.2 | 23.8 | 0.0 | 6.3 | 67.6 |
| | PPSU 150 cycles | 86.8 | −0.4 | 24.1 | 1.8 | 7.2 | 71.0 |
| | PPSU 300 cycles | 76.5 | 5.9 | 60.7 | 38.3 | 22.5 | 53.1 |
| Ex. 9 | PEI as molded | 85.9 | −4.7 | 51.2 | 0.0 | 1.2 | 69.8 |
| | PEI 150 cycles | 87.4 | −5.6 | 50.2 | 2.0 | 1.6 | 72.9 |
| | PEI 300 cycles | 87.7 | −5.4 | 49.6 | 2.5 | 3.3 | 73.4 |

While the invention has been described with reference to several embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A sterilized article comprising a sterilized polyetherimide polymer composition having an as molded color, wherein after exposure to 100 cycles of the hydrogen peroxide plasma sterilization using a mixture of hydrogen peroxide vapor and hydrogen peroxide plasma for 30 minutes at 20 to 55° C., the color of the polymer composition exhibits a color shift of delta E of 10 units or less relative to the as molded color of the polymer composition before the first hydrogen peroxide plasma sterilization cycle, wherein delta E is measured in accordance with ASTM D2244, wherein the polyetherimide has less than 100 ppm amine end groups.

2. The sterilized article of claim 1, wherein the delta E of the polymer composition after the exposure of the article to 100 cycles of hydrogen peroxide plasma sterilization is less than 5 units.

3. The sterilized article of claim 1, wherein the delta E of the polymer composition is 10 units or less after exposure of the article to 100 to 200 sterilization cycles, wherein each cycle is from 10 to 60 minutes at 20 to 55° C.

4. The sterilized article of claim 2, wherein the delta E of the polymer composition after the exposure is less than 5 units.

5. The sterilized article of claim 1, wherein the article has a tensile strength at yield after 150 cycles of a treatment of a member selected from the group of hydrogen peroxide plasma, hydrogen peroxide vapor, and combinations thereof, is at least 12000 psi.

6. The sterilized article of claim 1, wherein at least a portion of the polymer composition of the article has an etching, and wherein the etching is legible when observed from a distance of 0.3 meters without magnification after the exposure of the article to 100 cycles of hydrogen peroxide plasma sterilization.

7. The sterilized article of claim 6, wherein the etching is legible when observed from a distance of 0.3 meters without magnification after exposure of the article to 100 to 200 sterilization cycles, wherein each cycle is from 10 to 60 minutes at 20 to 55° C.

8. The sterilized article of claim 1, wherein the polyetherimide has less than 5 ppm of free bisphenol A.

9. The sterilized article of claim 1, wherein the polyetherimide comprises less than 50 ppm amine end groups.

10. The sterilized article of claim 1, wherein the polymer composition further comprises, based on the weight of the polymer composition, 0.1 to 10.0 weight percent of a colorant selected from rutile titanium dioxide, anatase titanium dioxide, coated titanium dioxide, passivated titanium dioxide, and encapsulated titanium dioxide, wherein the titanium dioxide has a particle size of from 0.1 to 10 micrometers.

11. The sterilized article of claim 10, wherein the polymer composition further comprises a colorant selected from the group consisting of: carbon black, solvent red 52, solvent violet 36, solvent violet 13, pigment brown 24, pigment blue 29, pigment blue 15:4, or combinations thereof.

12. The sterilized article of claim 1, wherein the polymer composition further comprises, based on the weight of the polymer composition, at least 0.01 weight percent of a phosphorous containing stabilizer having a molecular weight of at least 300 Daltons.

13. The sterilized article of claim 12, wherein the phosphorous containing stabilizer is selected from aryl phosphites and aryl phosphonates.

14. The sterilized article of claim 1, wherein the polymer composition further comprises, based on the weight of the polymer composition, at least 0.05 weight percent of a mold release agent selected from: C6 to C36 alkyl carboxylic esters, C6 to C36 alkyl carboxylic acids, C6 to C36 alkyl carboxylic acid salts, C6 to C36 alkyl amides, and polyolefins.

15. The sterilized article of claim 1, wherein the article is selected from a molded part, sheet, slab, profile, film, and fiber.

16. The sterilized article of claim 15, wherein the article is selected from a medical device, surgical device, sterilization device, decontamination device, food handling device, food preparation device, beverage handling device, beverage preparation device, or a component thereof.

17. The sterilized article of claim 16, wherein the article is selected from a container, a syringe body, a tray, an animal cage, an endoscope, a ureteroscope, a catheter, a clamp, a cable, a telescope, forceps, scissors, and a drill.

18. The sterilized article of claim 1, wherein the article further comprises a biocide.

19. The sterilized article of claim 18, wherein the biocide is selected from metals, inorganic compounds, and organic compounds.

20. The sterilized article of claim 18, wherein the biocide is selected from germicides, antimicrobials, antibiotics, antibacterials, antiyeasts, antialgals, antivirals, antifungals, antiprotozoals, antiparasites, and combinations thereof.

21. The sterilized article of claim 1, wherein polyetherimide comprises repeating units of the formula

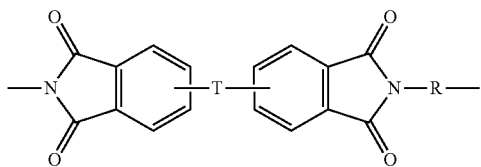

wherein R is a divalent radical of the formulae

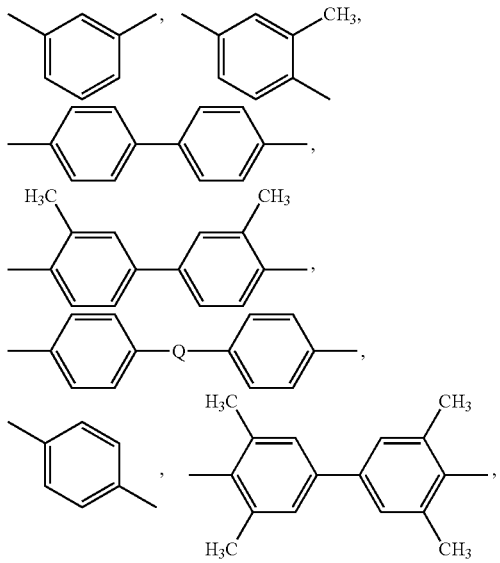

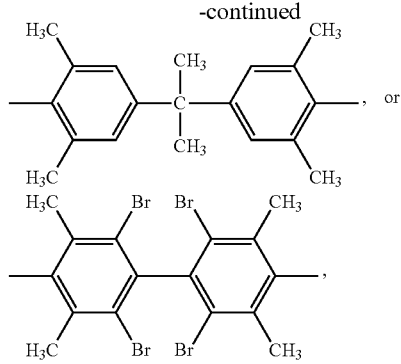

or combinations thereof wherein Q is selected from —O—, —S—, —C(O)—, —SO$_2$—, —SO—, and —C$_y$H$_{2y}$— wherein y is an integer from 1 to 5; and T is —O— or a group of the formula —O—Z—O— wherein the divalent bonds of the —O— or the —O—Z—O— group are in the 3,3', 3,4', 4,3', or the 4,4' positions and Z is a divalent group of the formula

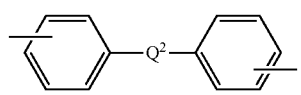

wherein Q$^2$ is selected from —O—, —S—, —C(O)—, —SO$_2$—, —SO—, and —C$_y$H$_{2y}$— wherein y is an integer from 1 to 5.

22. A sterilized article comprising a sterilized polymer composition having an as molded color, the polymer composition comprising a polyetherimide, treated with a member selected from hydrogen peroxide plasma, hydrogen peroxide vapor, and combinations thereof;

wherein the polyetherimide has a weight average molecular weight of 10,000 to 80,000 Daltons;

wherein after exposure to 100 cycles of sterilization for 30 minutes at 20 to 55° C., the color of polymer composition of the article exhibits a color shift of delta E of 10 units or less relative to the as molded color of the polymer composition before the first hydrogen peroxide sterilization cycle, wherein delta E is measured in accordance with ASTM D2244;

wherein at least a portion of the sterilized polymer composition has an etching, wherein the etching is legible when observed from a distance of 0.3 meters without magnification after the exposure of the article to 100 cycles of the hydrogen peroxide sterilization.

* * * * *